United States Patent
Gatzemeyer et al.

(10) Patent No.: US 7,140,058 B2
(45) Date of Patent: *Nov. 28, 2006

(54) TOOTHBRUSH WITH KINETIC PLATE

(75) Inventors: John J. Gatzemeyer, Hillsborough, NJ (US); Eduardo J. Jimenez, Manalapan, NJ (US); Eyal Eliav, New York, NY (US)

(73) Assignee: Colgate-Palmolive Company, New York, NY (US)

( * ) Notice: Subject to any disclaimer, the term of this patent is extended or adjusted under 35 U.S.C. 154(b) by 488 days.

This patent is subject to a terminal disclaimer.

(21) Appl. No.: 10/260,585

(22) Filed: Sep. 27, 2002

(65) Prior Publication Data

US 2004/0060135 A1 Apr. 1, 2004

(51) Int. Cl.
*A61C 17/22* (2006.01)

(52) U.S. Cl. .............................. 15/22.1; 15/28; 15/110; 601/142

(58) Field of Classification Search .................. 15/22.1, 15/22.2, 22.4, 28, 110; 601/142
See application file for complete search history.

(56) References Cited

U.S. PATENT DOCUMENTS

| | | | | |
|---|---|---|---|---|
| 2,206,726 A | * | 7/1940 | Lasater | ........................ 15/188 |
| 4,368,272 A | | 1/1983 | Kashket | |
| 5,353,460 A | * | 10/1994 | Bauman | ........................ 15/22.1 |
| 5,524,312 A | | 6/1996 | Tan et al. | |
| 5,617,603 A | | 4/1997 | Mei | |
| 5,625,916 A | | 5/1997 | McDougall | |
| 5,628,082 A | | 5/1997 | Moskovich | |
| 6,000,083 A | | 12/1999 | Blaustein et al. | |
| 6,446,295 B1 | * | 9/2002 | Calabrese | ........................ 15/28 |
| 6,785,929 B1 | | 9/2004 | Fritsch et al. | |
| 2001/0020314 A1 | | 9/2001 | Calabrese | |
| 2001/0023516 A1 | | 9/2001 | Driesen et al. | |
| 2003/0066145 A1 | * | 4/2003 | Prineppi | ........................ 15/22.1 |
| 2003/0084524 A1 | | 5/2003 | Blaustein et al. | |
| 2003/0084525 A1 | * | 5/2003 | Blaustein et al. | ............ 15/22.1 |
| 2003/0140437 A1 | | 7/2003 | Eliav et al. | |
| 2004/0143917 A1 | * | 7/2004 | Ek | .............................. 15/22.1 |

FOREIGN PATENT DOCUMENTS

| | | | |
|---|---|---|---|
| GB | 2319170 | * | 5/1998 |
| JP | 9-140456 | * | 6/1997 |

* cited by examiner

*Primary Examiner*—Mark Spisich
(74) *Attorney, Agent, or Firm*—Ellen K. Park

(57) ABSTRACT

A powered toothbrush is provided and includes a handle portion having a neck formed at one end and a head coupled to neck. The head includes a first carrier that is coupled to the head and is operatively connected to a first drive for moving the first carrier in a first direction. The first carrier has bristles, elastomeric cleaning members, or a combination thereof extending outwardly therefrom. The head also includes a second carrier that is coupled to the head and is in selective engagement with a protrusion extending in a recess defined by the first carrier to impart movement in a second direction. The second carrier has bristles, elastomeric cleaning members or a combination thereof extending outwardly therefrom. In an exemplary embodiment, the first carrier oscillates in a rotational direction and the second carrier moves in a direction parallel to the head.

38 Claims, 11 Drawing Sheets

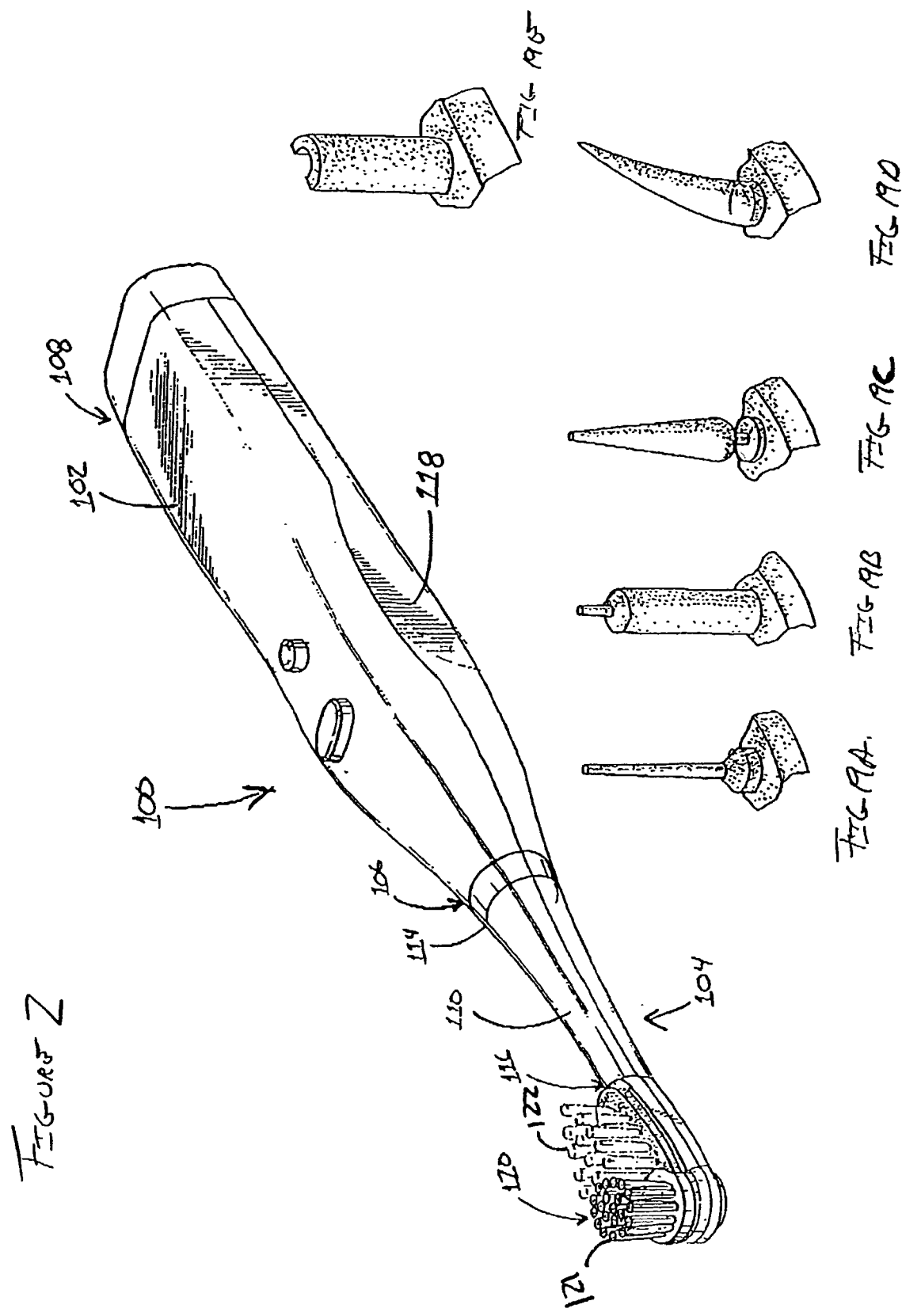

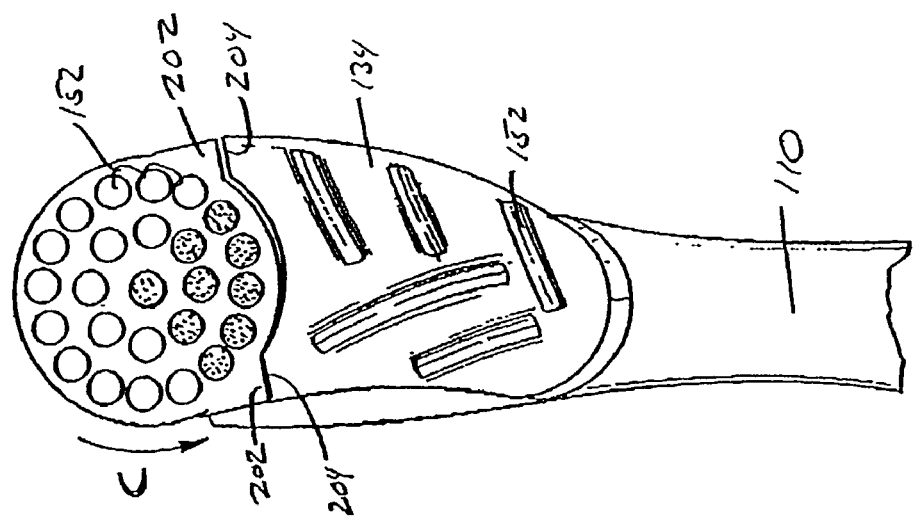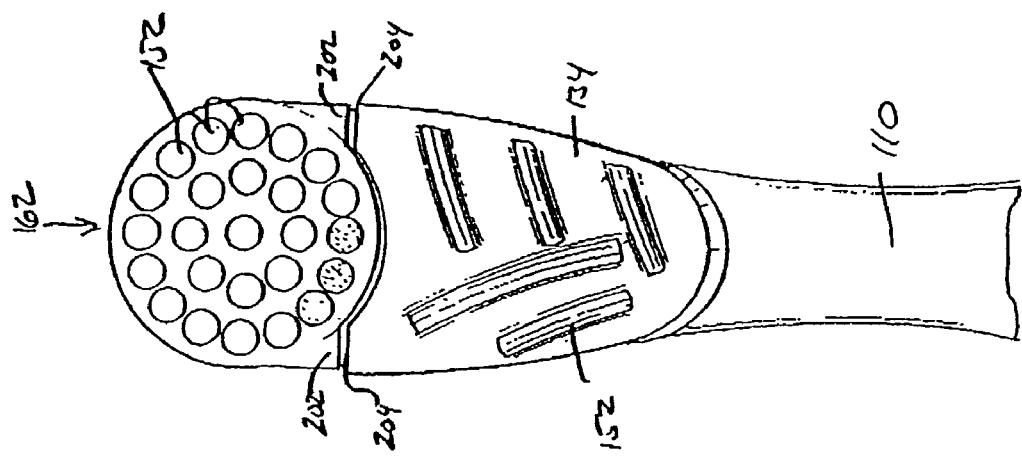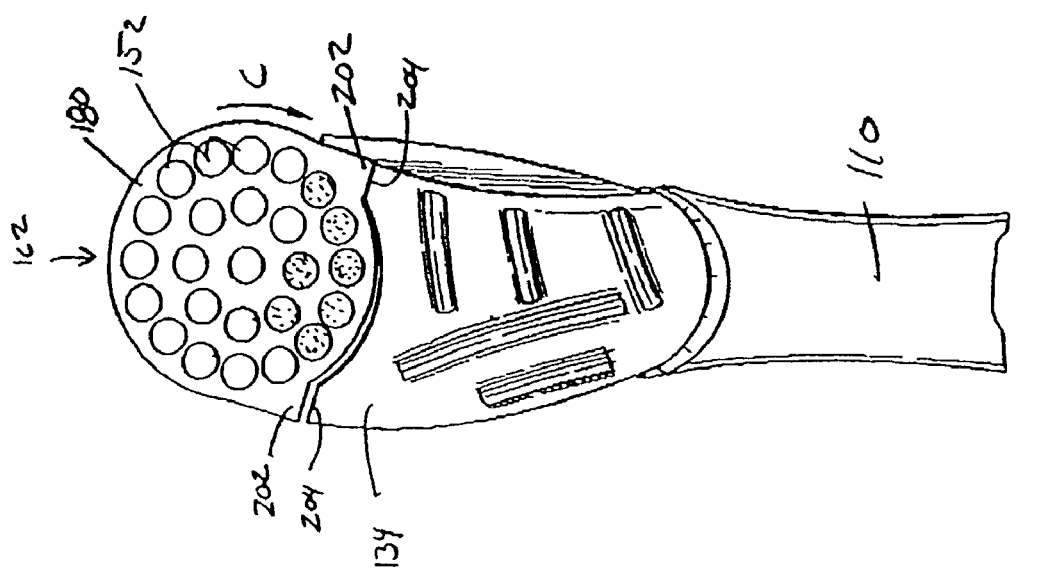

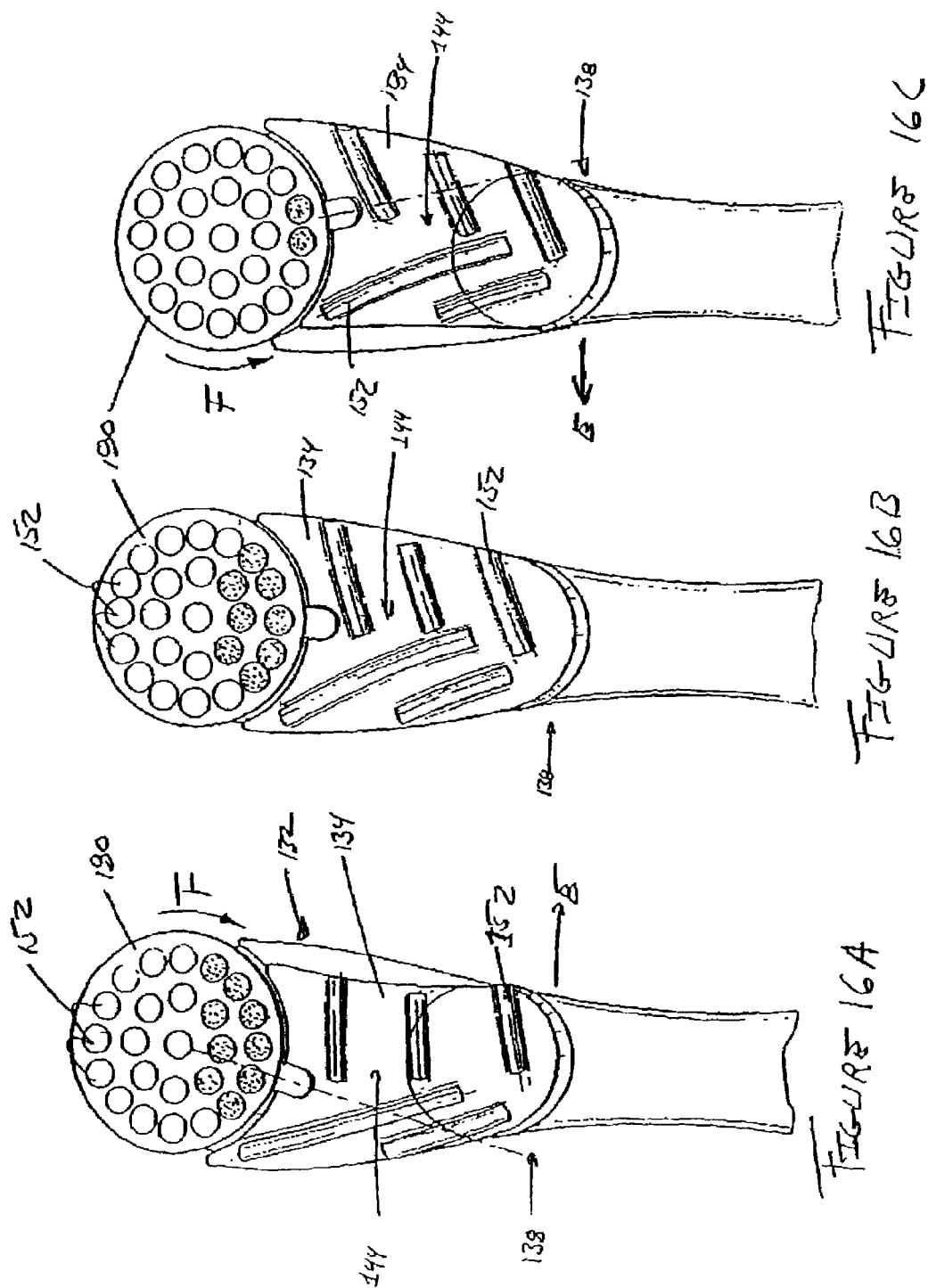

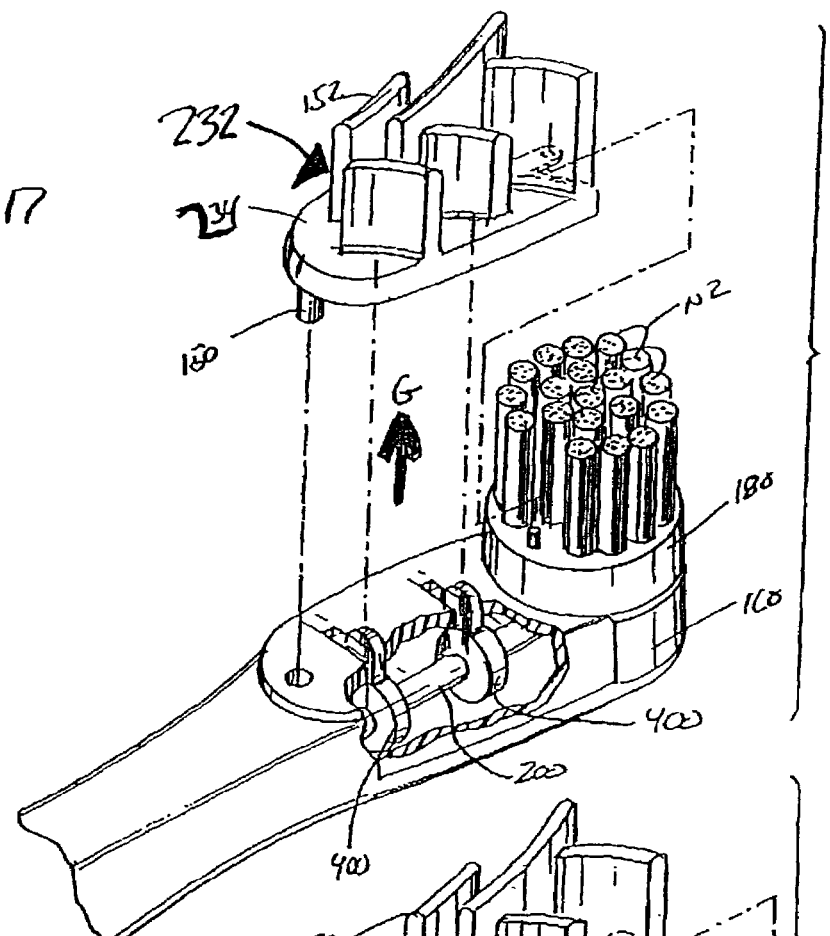
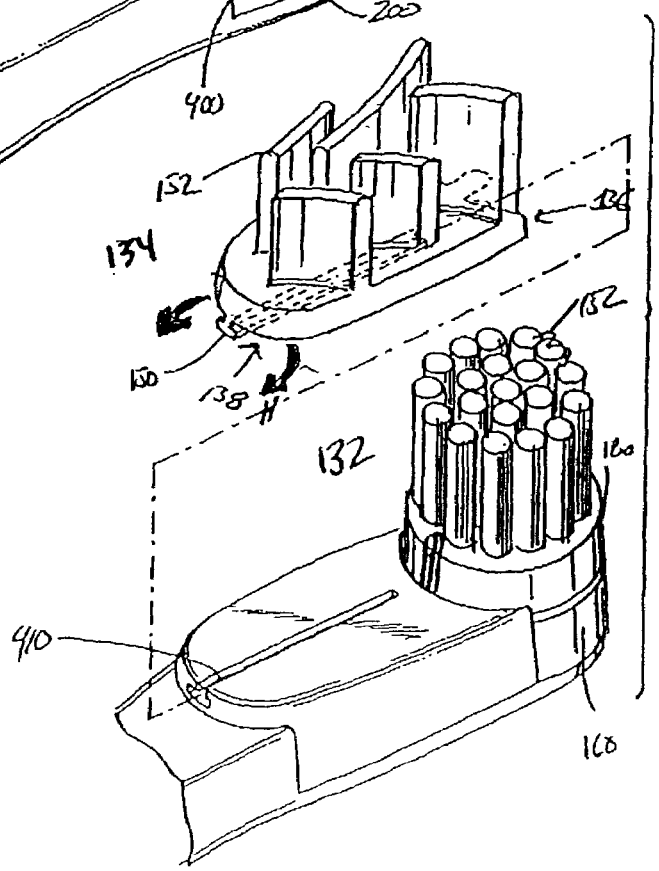

TOOTHBRUSH WITH KINETIC PLATE

BACKGROUND OF THE INVENTION

1. Field of the Invention

The present invention relates to powered toothbrushes, and more particularly, to a toothbrush having a head with two distinct moving sections that each provide oral health benefits to the user.

2. Discussion of Related Art

Toothbrushes provide many oral hygiene benefits. For example, toothbrushes remove plaque and food debris to help avoid tooth decay and disease. They remove stained pellicle from the surface of each tooth to help whiten the teeth. Also, the bristles combined with the brushing motion massage the gingival tissue for stimulation and increased health of the tissue.

Powered toothbrushes have been available for some time. Powered toothbrushes have advantages over manual (non-powered) toothbrushes in that they impart movement to the bristles at much higher speeds than possible manually. They also may impart different types and directions of motion. These motions, generally in combination with manual movement of toothbrush by the user, provide superior cleaning than manual toothbrushes. Typically, powered toothbrushes are powered by disposable or rechargeable batteries that power an electric motor that in turn drives toothbrush head.

Known powered toothbrushes include a brush head with a bristle carrier portion that rotates, oscillates or vibrates in some manner so as to clean the teeth. The bristles, which typically comprise bristle tufts, are generally uniform with one end fixed into the bristle carrier portion and the other end free to contact the surface of the teeth while brushing. The free ends of the various tufts present a surface envelope that is capable of some deformation when the bristles bend. When in contact with the surface to be brushed, the bristles may deform so that the surface envelope tends to conform to the complex surface of the teeth. Human teeth generally lie in a "C" shaped curve within the upper and lower jaw, and each row of teeth consequently has a convex outer curve and a concave inner curve. Individual teeth often have extremely complex surfaces, with areas that may be flat, concave, or convex. The more precise conformation between the bristles and the tooth surface, the more effective toothbrush may be in cleaning, whitening and/or stimulating.

Known powered toothbrushes typically arrange the bristles in a compact conical or cylindrical pattern on a generally circular, disk-shaped bristle carrier. The powered toothbrush heads are traditionally compact, generally oval in shape and heads are produced with a flat trimmed bristle pattern. Alternatively, other head shapes and bristle patterns are available.

One example of a powered toothbrush is depicted in U.S. Pat. No. 5,625,916 to McDougall, which is hereby incorporated by reference in its entirety. Toothbrush shown in McDougall has a disc-shaped bristle carrier. The bristle carrier, and thus the bristles, are driven in a vibrating or oscillating manner. This type of toothbrush is described herein with reference to FIGS. 1A–1C. A toothbrush 5 includes a handle portion 10 at a proximal end of toothbrush 5 and a head 11 at a distal end of toothbrush 5. Handle portion 10 has compartments for containing a powered motor 14 and batteries 15 and 16. Head 11 includes a generally circular bristle holder (carrier) 13. A rotatable shaft 12 extends from the motor 14 to head 11. A shaft coupling 17 may be located along the shaft 12 and configured to provide for the shaft 12 to be separated at a point between the motor 14 and head 11. This permits the shaft to be removed from toothbrush 5, e.g., for cleaning, servicing, or replacement.

Head 11 includes a post 18 that provides a rotational pivot axis for the bristle holder 13 containing bristle tufts 19. The distal end of the shaft 12 has a journal or offset 20 that is radially displaced from the longitudinal axis of the shaft 12, which may be integrally formed therewith. The bristle holder 13 has a slot 22 that receives the offset 20. The offset 20 and slot 22 are configured so as to be oriented toward the intersection of the shaft 12 axis and the longitudinal axis of the post 18. When the motor 14 rotates the shaft 12, the motion of the offset 20 defines a circle about the shaft 12 axis and drivingly engages slot 22 such that the bristle holder 13 vibrates or oscillates about the post 18 axis through a rotational angle A. The rotational angle A is defined by the displacement of the offset 20 from the shaft 12 axis relative to the diameter of the bristle holder 13.

Although powered toothbrushes such as those described immediately above provide advantages over manual toothbrushes, they are subject to various limitations. Providing a rotating or oscillating bristle holder (carrier) with a typical oblong or oval toothbrush head constrains the size of the moving bristle holder, and consequently the area of bristles available for teeth cleaning. Also, when the bristles are placed in contact with the teeth during brushing, there is less bristle contact with adjacent areas, such as the gums. Thus, while these compact bristle patterns provide for cleaning, there is minimal whitening and stimulation.

One attempt to overcome the limitations associated with a small powered bristle area is shown in U.S. Pat. No. 6,000,083 to Blaustein et al. The toothbrush in Blaustein et al. has a bristle area and pattern similar to a manual toothbrush, but an area of the bristles has simply been replaced by a powered bristle section. The result is that the head has a powered or moving bristle section and static bristle section. The limitation of Blaustein et al. is that the static bristle section provides no better cleaning, whitening or stimulation than a manual toothbrush.

International Application No. PCT/EPO1/07615 of Braun GmbH discloses a powered toothbrush with two separate bristle parts that can move. Each bristle part can have a different range and/or type of motion. However, only one bristle part is powered. The other unpowered bristle part moves due to a resonance effect imparted by the frequency of the movement of the first bristle part.

This free resonance causes a number of difficulties. First, because any contact between the bristle parts will dampen or cancel any resonance of the unpowered bristle part, the unpowered bristle part "floats" separately from the powered bristle part. This necessitates separation or gaps between them. These gaps expose the internal workings of the head to foreign matter such as water, saliva, toothpaste, and food particles. This foreign matter may interfere with the workings of the unpowered bristle head. For example, the unpowered bristle part is spring-loaded to assist its resonance. Foreign matter may accumulate on or around the spring, interfering with its function. In addition, food particles may remain in the head and may fester and host microorganisms, which are undesirable if not potentially harmful when introduced directly into the mouth.

Another limitation of such a design is that movement of the unpowered bristle part may be damped by contact with the teeth, or lessened when the frequency of the powered part shifts from the resonance frequency. This can occur due to pressure imparted against the powered bristle part by the teeth or gums during brushing. Finally, the energy imparted to the unpowered bristle part is only a portion of the energy input into the powered part. Therefore, the unpowered bristle part is less effective in cleaning than the powered part, limiting the overall effectiveness of the toothbrush.

Thus, there is a need in the art for a powered toothbrush with increased effectiveness through a larger area of powered or driven bristles or bristles that are otherwise movable. There is also a need for a toothbrush having increased whitening and/or stimulation than known toothbrushes. There is further a need for such improved toothbrushes to be comparable in manufacturing and purchasing costs as known powered toothbrushes.

SUMMARY OF THE INVENTION

A powered toothbrush is provided and includes a handle portion at a proximal end and either a fixed head or a linkage for receiving a removable head at a distal end thereof. A neck is further formed between handle portion and head. According to one embodiment of the invention, the head includes two distinct movable parts that each and together provide oral health benefits, each being adapted to have a number of bristles or elastomeric cleaning members extending therefrom adapted to contact surfaces of one or more teeth and surrounding areas. The powered toothbrush is further formed with a drive mechanism that imparts movement to the first movable part to deliver a cleaning, polishing, whitening action that supplements the cleaning efficiency of a typical powered toothbrush. The first movable part in turn imparts movement to the second movable part.

In one embodiment, the first movable head part is a first bristle carrier that supports a number of bristle tufts, elastomeric cleaning members, or a combination thereof. The first bristle carrier is operatively mounted to head and is coupled to the drive mechanism such that the first bristle carrier oscillates back and forth in a direction parallel to toothbrush head. Preferably, the oscillating first bristle carrier is moved back and forth in a rotational direction. The second movable part is formed as a second carrier that includes an elastomeric platform that is operatively fixedly mounted at at least one portion thereof to the head and is selectively engaged by the first carrier to provide movement. The second carrier thus oscillates and translates in a direction parallel and longitudinal to the head, thereby providing a moving head section in addition to the oscillating section that is formed by the first bristle carrier.

Other features and advantages of the present invention will be apparent from the foregoing detailed description when read in conjunction with the accompanying drawings.

The invention accordingly comprises the several steps and the relation of one or more of such steps with respect to each of the others, and the apparatus embodying features of construction, combination(s) of elements and arrangement of parts that are adapted to effect such steps, all as exemplified in the following detailed disclosure, and the scope of the invention will be indicated in the claims.

BRIEF DESCRIPTION OF THE DRAWING FIGURES

For a more complete understanding of the invention, reference is made to the following description and accompanying drawings, in which:

FIG. 2 is a front and side perspective view of a powered toothbrush according to one exemplary embodiment of the invention showing a toothbrush head having distinct first and second movable sections constructed in accordance with the invention;

FIGS. 13A–13C are front views of the powered toothbrush head of FIG. 11 in various positions generated when in motion;

FIGS. 16A–16C are front views of the powered toothbrush head of FIG. 15 in various positions generated when in motion;

FIG. 17 is a front and side exploded cut-away perspective view of another embodiment of a powered toothbrush head of the powered toothbrush of FIG. 2;

FIG. 18 is a front and side perspective exploded view of another embodiment of a powered toothbrush head of the powered toothbrush of FIG. 2;

FIG. 19A is a perspective view of an elastomeric tooth care element having a first configuration and adapted for use in a toothbrush head constructed in accordance with the invention;

FIG. 19B is a perspective view of an elastomeric tooth care element having a second configuration and adapted for use in a toothbrush head constructed in accordance with the invention;

FIG. 19C is a perspective view of an elastomeric tooth care element having a third configuration and adapted for use in a toothbrush head constructed in accordance with the invention;

FIG. 19D is a perspective view of an elastomeric tooth care element having a fourth configuration and adapted for use in a toothbrush head constructed in accordance with the invention; and FIG. 19E is a perspective view of an elastomeric tooth care element having a fifth configuration and adapted for use in a toothbrush head constructed in accordance with the invention.

DETAILED DESCRIPTION OF THE PREFERRED EMBODIMENT

Figure 1A:
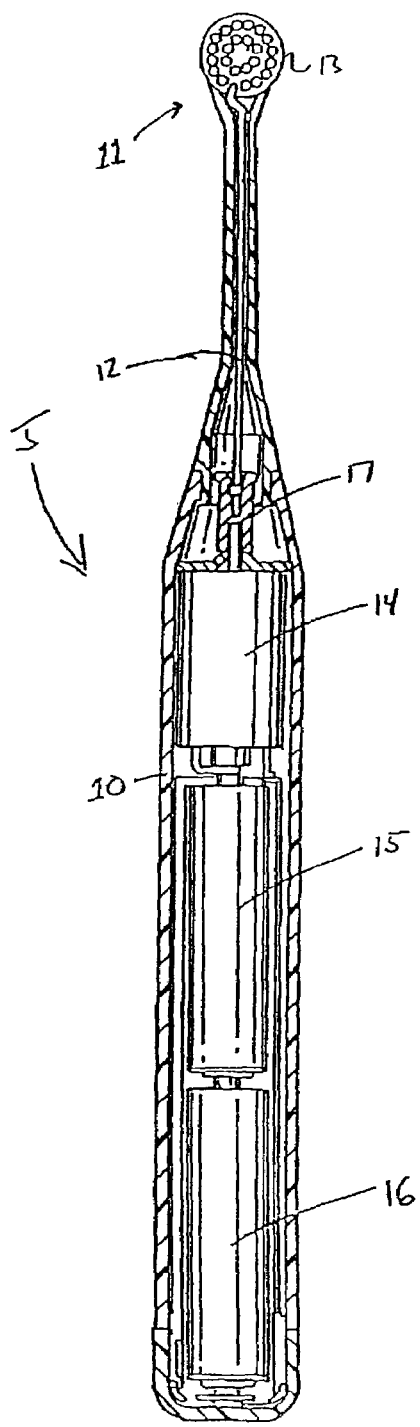
FIG. 1A, is a front partial cross-sectional view of a conventional powered toothbrush including a head.
Figure 1B:
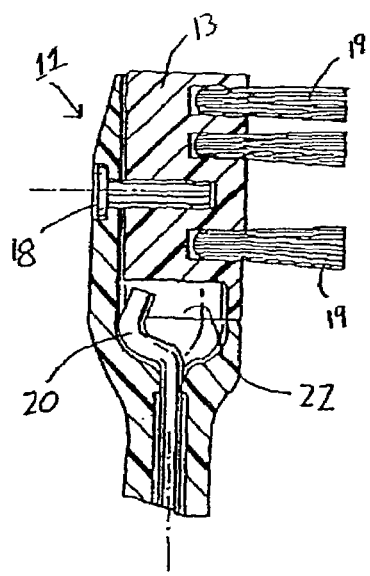
FIG. 1B is a partial side cross-sectional view of toothbrush head of FIG. 1A.
Figure 1C:
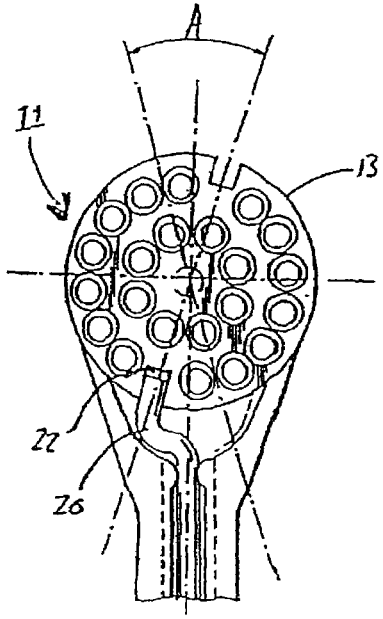
FIG. 1C is a partial front cross-sectional view of toothbrush head of FIG. 1A.

Referring first to FIG. 2, an exemplary powered toothbrush according to a first embodiment of the invention is illustrated and generally indicated at 100. Toothbrush 100 includes a handle 102 at a proximal end thereof that defines an interior compartment (not illustrated) for housing various toothbrush components, and a brush section 104 that is defined by a neck 110 that terminates in a head 120 at a distal end of toothbrush 100. Handle 102 has a free proximal end 108 and an opposite neck end 106. Neck 110 generally includes a first end 114 and a second end 116 with first end 114 being located at neck end 106 of handle 102 and the second end 116 being located at head 120. In other words, neck 110 is the portion of toothbrush 100 that extends between handle 102 and head 120. Neck 110 also defines an interior compartment (not shown) for housing various working components of toothbrush 100. Head 120 is preferably generally aligned with the longitudinal axis of toothbrush 100.

Neck 110 and handle 102 may be constructed as a unitary member by forming neck 110 integral to handle 102 at neck end 106 of handle 102, or may be formed detachable from handle 102 at neck end 106 of neck 110. In accordance with this detachable embodiment, the combined neck 110 and head 120 can be removed from handle 102 to permit cleaning, servicing and/or interchanging of either handle 102 or the combined neck 110 and head 120 (brush section 104). When neck 110 is formed to be detachable from handle 102, first neck end 114 preferably includes a connector linkage (not illustrated) that is adapted to be detachably joined to handle 102 using traditional techniques. It will also be appreciated that the point of detachment may be between head 120 and neck 110 such that head 120 is of a refill head type. Furthermore, head 120 is formed of a first bristle carrier 121 and a second bristle carrier 122.

It will further be appreciated that the illustrated shapes of handle 102 and neck 110 are merely exemplary in nature and handle 102 and/or neck 110 can be formed to have any number of shapes. Preferably, the shapes of handle 102 and neck 110 are ergonomically pleasing to a user of toothbrush 100 and provide a toothbrush that is easily gripped and held and easily manipulated by the user. For example, handle 102 may include slightly recessed finger sections 118 which are formed on opposite sides of handle 102. One recessed finger section 118 is designed to receive the thumb of one hand and the other recessed finger section 118 is designed to receive one or more other fingers of the same hand to thereby assist the user in proper placement of toothbrush 100 in the user's hand. One or more of recessed finger sections 118 may include ribs or another type of roughened surface to assist the user in gripping toothbrush 100 at recessed finger sections 118.

Figure 3:
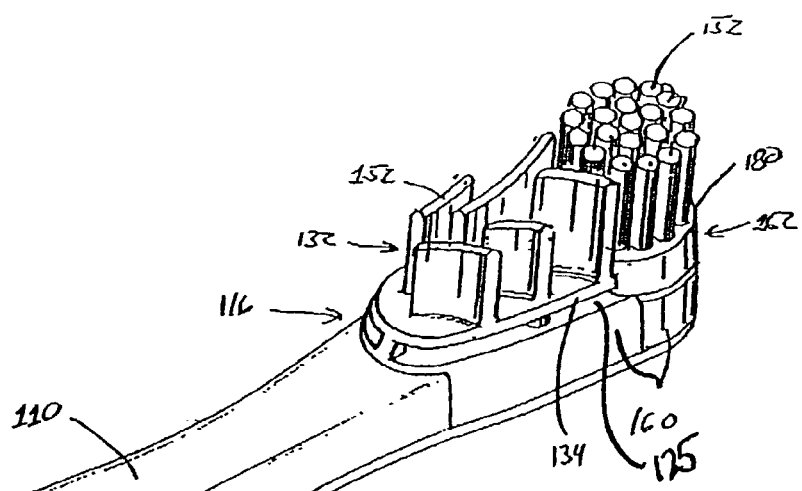
FIG. 3 is a front and side perspective view of a powered toothbrush head according to another exemplary embodiment of a powered toothbrush constructed in accordance with the invention.
Figure 4:
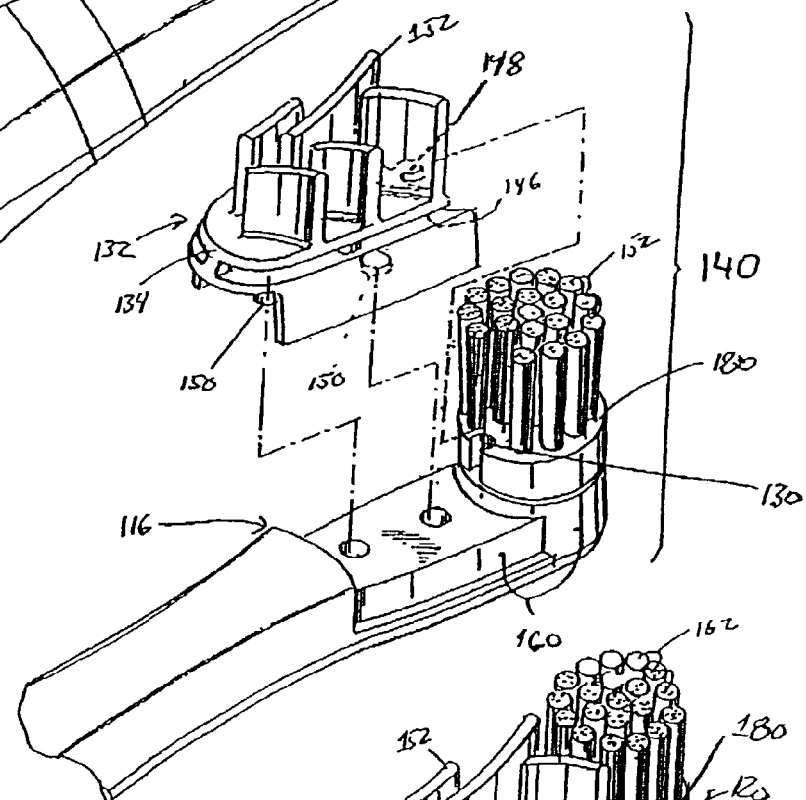
FIG. 4 is a front and side perspective exploded view of the powered toothbrush head of the powered toothbrush of FIG. 3.
Figure 5:
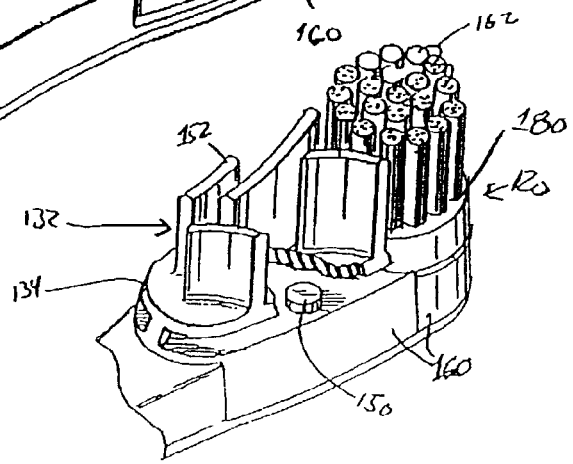
FIG. 5 is a front and side perspective cutaway view of the powered toothbrush head of the powered toothbrush of FIG. 3.

Referring next to FIGS. 3–5, an additional embodiment of a powered toothbrush head is shown. A head 120 of toothbrush 100 includes a head base 160 that partially defines an inner compartment 125 of head 120. Head base 160 may be constructed so that it terminates in a rounded distal end 162, which also defines the distal end of toothbrush 100. Preferably, head base 160 is integrally attached to second end 116 of neck 110.

Head 140 also includes a first movable bristle carrier 180 which is illustrated as being at the outermost or distal portion of head 140. First bristle carrier 180 may have a construction that is either identical to or similar to that of the bristle holders 13 or 121 illustrated in FIGS. 1A–1C and FIG. 2. First movable bristle carrier 180 is preferably formed with a disk having circular cross-section since it is intended to oscillate in a rotational manner about a center point thereof; first movable bristle carrier 180 is formed defining a recess 130 directed toward a second movable bristle carrier 132. However, it will be appreciated that first movable bristle carrier 180 is not limited to having a disk shape and can have any number of different shapes, such as an oval or various other regular or irregular shapes, so long as first moveable bristle carrier 180 is able to oscillate in a substantially rotational manner. A circular shape is preferred since it requires the least amount of clearance to accommodate the oscillating movement.

A plurality of tooth care elements 152 are coupled to and extend outwardly from first movable bristle carrier 180 in a direction substantially perpendicular to a plane defined by a face of first movable bristle carrier 180. As used herein, the term "tooth care elements" includes any type of structure that is commonly used or is suitable for use in providing oral health benefits (e.g., tooth cleaning, tooth polishing, tooth whitening, etc.) by making intimate contact with surfaces of the teeth and surrounding areas. Such tooth care elements include but are not limited to tufts of bristles that can be formed to have a number of different shapes and sizes, and various elastomeric members (see FIGS. 19A–19E) that can be formed to have a number of different shapes and sizes, or a combination of both. Bristle tufts arranged on first bristle carrier 180 is only one exemplary configuration and it will be understood that other bristle configurations (such as stapled, IMT, etc.) can be used. Bristle tufts may all be formed of the same or different bristle materials (such as nylon bristles, spiral bristles, rubber bristles, etc.) Moreover, while the tooth care elements can be arranged so that they are generally perpendicular to the face of first bristle carrier 180 (as noted above), some or all of the tooth care elements can be angled at various angles with respect to first bristle carrier 180 as desired. When first bristle carrier 180 includes bristle tufts, it is thereby possible to select the combination of bristles configurations, bristle lengths, bristle materials and bristle orientations to achieve specific intended results, such as to create as much movement from the moving tuft heads to deliver additional oral health benefits such as enhanced cleaning, tooth polishing and/or tooth whitening.

While first bristle carrier 180 has been defined as a movable bristle carrier 180, it will be understood that first movable carrier 180 is not limited to having only tufts of bristles as a part thereof. Instead, first movable carrier 180 is to be broadly considered as being a carrier for any number of suitable tooth care elements 152 or any number of combinations of different types of tooth care elements 152. For example, first movable carrier 180 may include a number of elastomeric members to provide the desired oral health benefits. The elastomeric members may be attached to first movable carrier 180 using conventional techniques, including integrally forming the elastomeric members with an upper surface of carrier 180. Tooth care elements 152 provided as part of first movable carrier 180 can thus be entirely of one type (e.g., bristle tufts or elastomeric members) or can be formed according to a mixed arrangement.

FIGS. 19A–19E illustrate various exemplary elastomeric members that may serve as tooth care elements 152. FIG. 19A shows an elastomeric tooth care element in the form of a thin spike; FIG. 19B shows an elastomeric tooth care element in the form of a barrel spike; FIG. 19C shows an elastomeric tooth care element in the form of a squeegee point; FIG. 19D shows an elastomeric tooth care element in the form of an angled point; and FIG. 19E shows an elastomeric tooth care element in the form of a section of an elastomeric wall. The elastomeric wall of FIG. 19E may be formed with a linear, planar shape; a zigzag shape; a serpentine shape, etc. All of the above elastomeric tooth care elements may be formed having smooth textures or can have rough surfaces. In addition, the wall sections of the elastomeric tooth care elements may be formed vertically straight, taper inward toward one end or expand toward one end. The tops of the elastomeric tooth care walls may be formed with a planar surface or a protrusion (i.e., hump) or the like formed thereat.

For purpose of illustration only, first movable carrier 180 will be described as containing a predetermined number of bristle tufts; however the following features apply equally to the situation where first movable carrier 180 is formed entirely or partly of elastomeric members. The bristle tufts of first movable carrier 180 may be formed with uniform heights or non-uniform heights. For example, first movable carrier 180 may include bristle tufts having a first height as well as bristle tufts having a second different height.

First movable bristle carrier 180 is constructed so as to pivotally rotate about a center point thereof, thereby effectuating movement of the bristle tufts and/or elastomeric members that extend outwardly from first movable bristle carrier 180. The movement of first movable bristle carrier 180 is preferably an oscillation type movement as first movable bristle carrier 180 pivots about a post at a center point thereof (see FIG. 1). First movable bristle carrier 180 is formed with a slot or opening (not illustrated). This slot is preferably identical to or substantially similar to slot 22 illustrated in FIGS. 1A–1C. Preferably, slot 22 is formed at a peripheral edge of first movable bristle carrier 180 and extends along a substantial height of first movable bristle carrier 180. For example, slot 22 preferably does not extend to the upper surface of first bristle carrier 180 where the tooth care elements are positioned. Instead, slot 22 preferably has a closed upper end to prevent foreign matter, such as saliva, toothpaste, foreign particles, etc., from entering slot when the operator is performing a brushing operation. The opposite end of slot 22 that is located within the inner compartment 125 of head 140 can be open.

Toothbrush 100 includes a drive mechanism to effectuate movement of certain parts of the toothbrush and more specifically, for causing movement of first movable bristle carrier 180. One exemplary drive mechanism is disclosed in U.S. Pat. No. 5,625,916 to McDougall, which has been previously incorporated herein by reference and includes a rotating drive shaft 200 that extends at least through neck 110 (i.e., the inner compartment thereof). Drive shaft 200 preferably has a construction that is the same as or similar in nature to shaft 12 illustrated in FIGS. 1A–1C.

Drive shaft 200 has one end (not illustrated) that is operatively connected to a drive member (not illustrated), such as a motor or any other type of drive device, for imparting movement to first movable bristle carrier 180. Drive shaft 200 is formed with an opposing distal end (not illustrated) that is bent such that the end is not axially aligned with the longitudinal axis of drive shaft 200. This distal end may be formed similar to the end 20 of FIGS. 1A–1C or may be formed differently so long as it performs the intended function. In other words, the end is an offset crank end of drive shaft 200 and is configured to be received in slot 22 so that a 360° rotational movement of shaft 200 is transmitted into an oscillating back and forth rotational movement of first movable bristle carrier 180.

The drive mechanism for powered toothbrush 100 can be any type of drive, e.g., a rotating drive, an oscillating drive, an eccentric drive, an unbalanced-generated drive, a drive having one more gearing mechanisms, and/or the like, that is capable of performing the intended function. The drive mechanism can be realized in the form of an electric motor or other type of motor and the movement generated by the drive can be imparted to one or more sections of head 140 (or 120) or to other elements that can be present at the brush section, such as bristle tufts, elastomeric members. The movement can be imparted directly through a driving axle, such as drive shaft 200 or it can be imparted through a driving post attached to the driving axle. When toothbrush 100 includes an oscillating drive mechanism either identical to or similar to the exemplary drive mechanism illustrated in FIGS. 1A through 1C, the interior compartment of handle 102 houses a motor operatively connected to drive shaft 200 and a source to power the motor, such as one or more batteries.

When the drive mechanism is actuated and drive shaft 200 is rotated, the movement of the crank end thereof imparts an oscillating back and forth movement of first movable bristle carrier 180 through an angle between about 10° to about 120° and in a preferred exemplary embodiment, the movement is through an angle between about 10° to about 30°, and in a most preferred embodiment is through an angle between about 10° to about 15°.

Figure 6C:
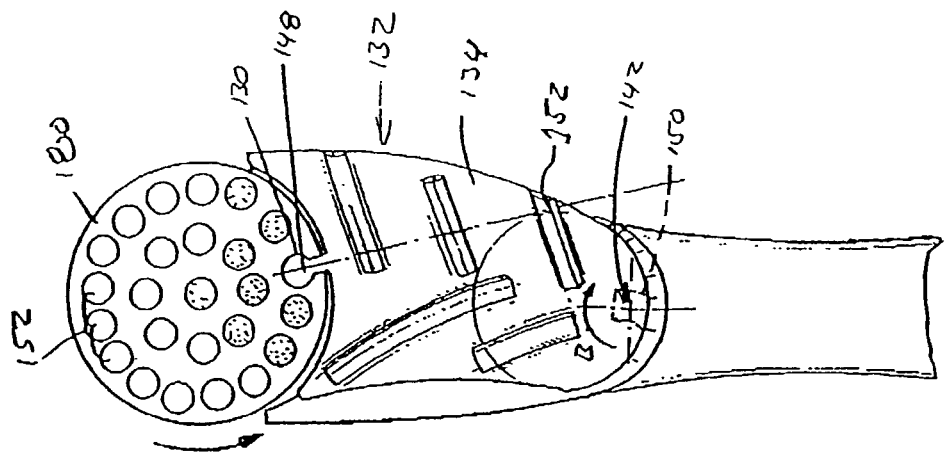
FIGS. 6A–6C are front views of the powered toothbrush head of FIG. 3 in various positions generated when in motion.
Figure 6B:
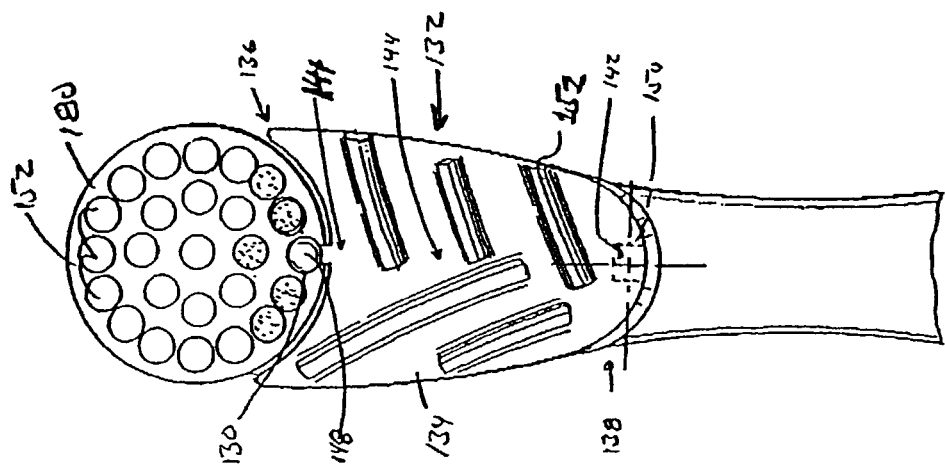
Figure 6A:
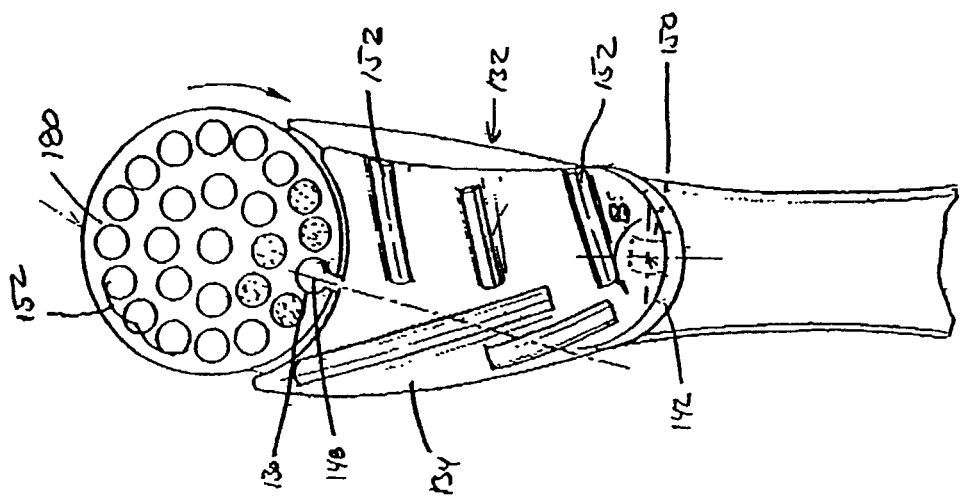

Referring next to FIGS. 6A, 6B and 6C in addition to FIGS. 3–5, toothbrush 100 (and head 140) further includes a second movable bristle carrier 132 that is operatively mounted on head 140. Second movable bristle carrier 132 comprises a platform 134 having at first end 136, a second end 138, a first end midpoint 141, a second end midpoint 142, a midpoint 144, and a bottom 146. A protrusion 148 extends outwardly from platform 134 at first end 136 thereof and is received into recess 130 of first movable bristle carrier 180, thereby providing a link between first carrier 180 and second carrier 132. In a preferred embodiment, a feature, such as at least one leg 150 is formed integral with platform 134 and is adapted to be received by head base 160 to support platform 134. It will be understood that the at least one leg 150 can have a number of different shapes and broadly, any member that can act as a support member can be used to couple platform 134 to head base 160.

There are numerous portions of the present invention, that when changed in accordance with various embodiments of the invention, will change the type and range of motion of both first movable bristle carrier 180 and second movable bristle carrier 132. The movement of first movable bristle carrier 180 is outlined above and can be altered by varying the drive or transmission of the motion of that drive to first movable bristle carrier 180. These variations are well known in the art.

Because movement of first movable bristle carrier 180 directly imparts movement to the platform 134 changes to the movement of first movable bristle carrier 180 will also change the movement of second movable bristle carrier 132. Additionally, changes in the structure and anchoring of second movable bristle carrier 132 can vary its movement as well. Various embodiments may be designed so that protrusion 148 of platform 134 is rigidly received in recess 130, or protrusion 148 may be frictionally received in recess 130.

Other changes to second movable bristle carrier may include that legs 150 and platform 134 may be formed from either a rigid or an elastomeric material. Different combinations of rigid or elastomeric legs 150 and platforms 134 will result in varied types and ranges of motion of platform 134. Another factor that will affect the type and range of the motion of platform 134 is the placement and number of the legs 150. In one of the preferred embodiments of the present invention, illustrated in FIGS. 6A–6C, is included one leg 150 formed integral platform 134 at about the second end midpoint 142 thereof. The movement of first movable bristle carrier 180 imparts a torsional movement on leg 150, as shown by arrow B and rotates platform 134 as well as imparts a lateral shift of first end 136 of second movable bristle carrier 132 parallel to the first end 136.

In other embodiments of the present invention, a first leg 150 is formed integral with platform 134 at the first end midpoint 141 thereof and/or a second leg 150 is formed integral with platform 134 at second end midpoint 142, as illustrated in FIGS. 3 through 5. A leg 150 may also be formed integral with platform 134 at midpoint 144 thereof, alone or in combination with other legs 150, as illustrated in FIGS. 7 through 10.

Figure 7:
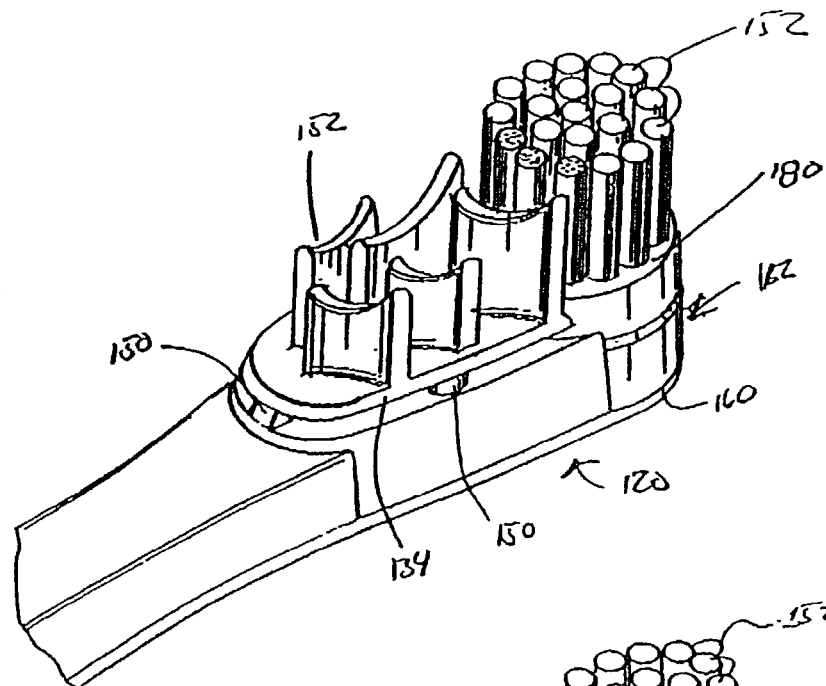
FIG. 7 is a front and side perspective view of another embodiment of a powered toothbrush head of the powered toothbrush of FIG. 2.
Figure 8:
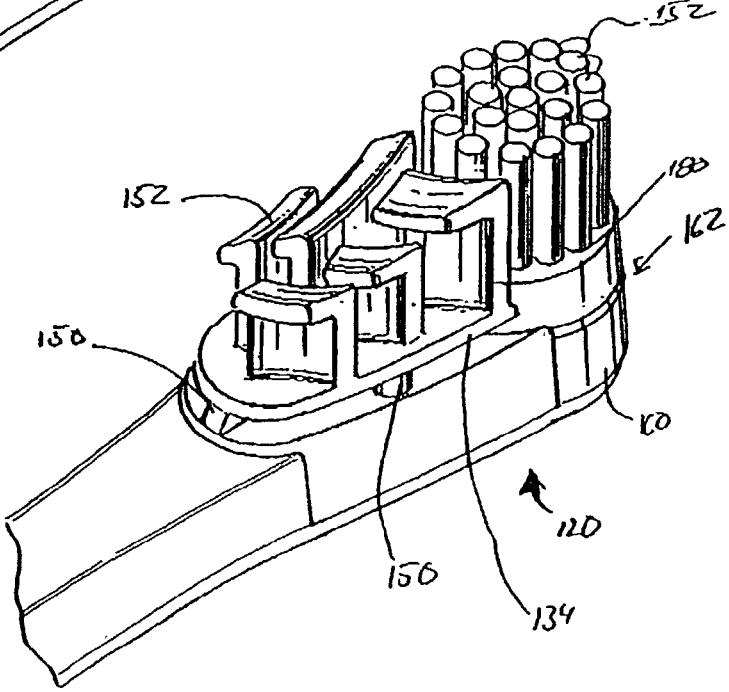
FIG. 8 is a front and side perspective view of another embodiment of a powered toothbrush head of the powered toothbrush of FIG. 2.
Figure 9:
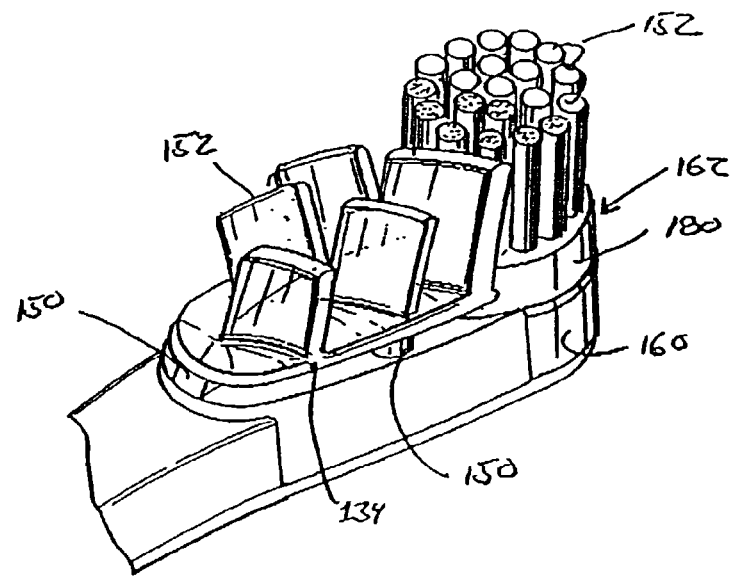
FIG. 9 is a front and side perspective view of another embodiment of a powered toothbrush head of the powered toothbrush of FIG. 2.
Figure 10:
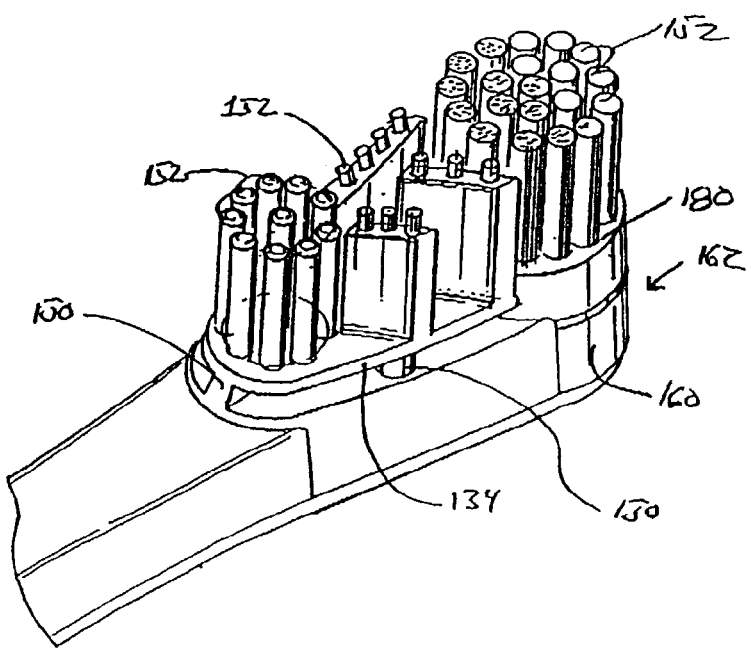
FIG. 10 is a front and side perspective view of another embodiment of a powered toothbrush head of the powered toothbrush of FIG. 2.

FIGS. 3–10 also illustrate differing variations and combinations of tooth care elements 152 including bristles and elastomeric tooth care elements. FIGS. 3–5 illustrate second movable bristle carrier being formed with short elastomeric walls in varying sizes and placement. FIG. 7 illustrates second movable bristle carrier being formed with short elastomeric walls having a top surface thereof being cupped. FIG. 8 illustrates second movable bristle carrier being formed with short elastomeric walls being formed with an overhang. FIG. 9 illustrates second movable bristle carrier being formed with short elastomeric walls that are not all erected parallel, but lean or curve to one side. Referring next to FIG. 10, the second movable bristle carrier contains a combination of short elastomeric walls with humps and a lower bristle section. The above variations are for illustration purposes only and it is realized that any combination of tooth care elements may be employed.

Figure 11:
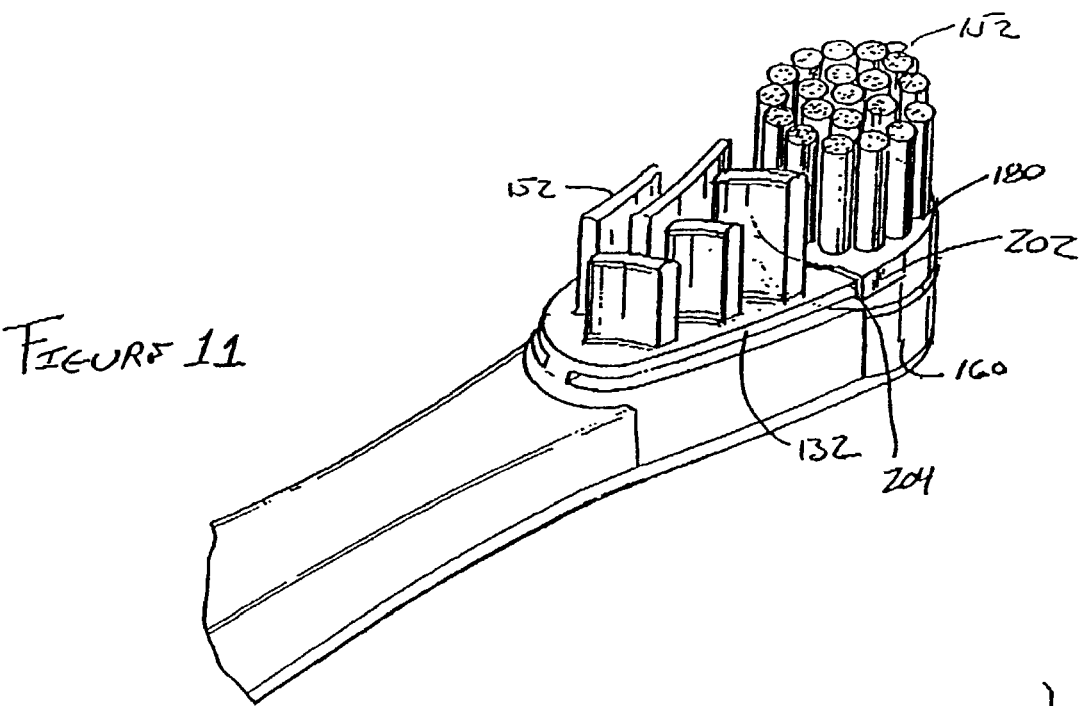
FIG. 11 is a front and side perspective view of another embodiment of a powered toothbrush head of the powered toothbrush of FIG. 2.
Figure 12:
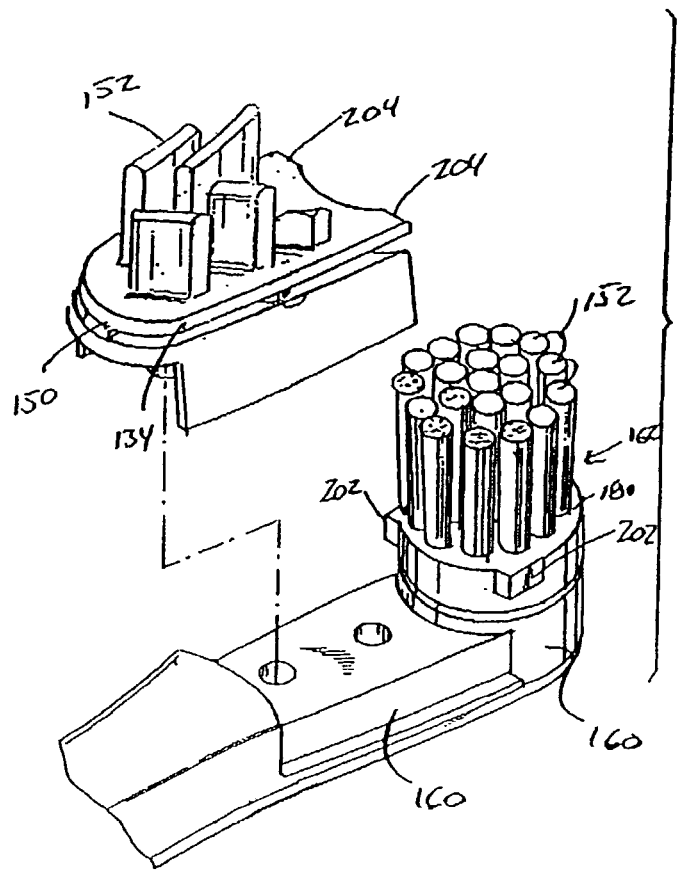
FIG. 12 is a front and side perspective exploded view of the embodiment of the powered toothbrush head of FIG. 11 of the powered toothbrush of FIG. 2.

FIGS. 11 through 13 illustrate an alternative embodiment of the invention utilizing head construction. The handle 102, neck 110, drive, and head base 160 may be formed similarly as described above. However in accordance with this embodiment of the invention first movable bristle carrier 180 is formed with one or more protrusions 202 directed toward platform 134 of second movable bristle carder 132. Platform 134 is formed similarly as described above, and further includes one or more protrusion contact points 204. The movement of first movable bristle carrier 180 imparts movement of platform 134 through contact of protrusions 202 with protrusion contact points 204. Again, as above, the material of leg 150 and platform 134, as well as the location of leg 150 will change the type and range of motion of second movable bristle carrier 132. FIGS. 13A through 13C illustrate an example of the movement first movable bristle carrier 180 may impart on platform 134. As first movable bristle carrier 180 rotates along arrow C, platform 134 is imparted a lateral shift of first end 136 parallel to first end 136 as well as a rotational shift in the direction of arrow C. While FIGS. 11–13 illustrate protrusions 202 not being connected to platform 134, it is also contemplated that protrusions 202 may be connected to platform 134 at protrusion contact points 204.

Figure 14:
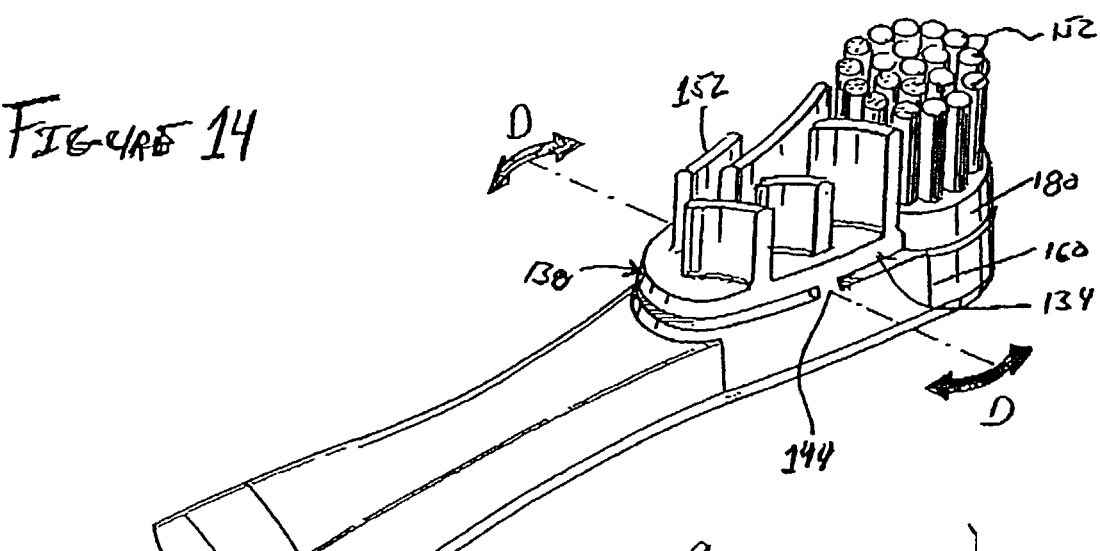
FIG. 14 is a front and side perspective view of another embodiment of a powered toothbrush head of the powered toothbrush of FIG. 2.
Figure 15:
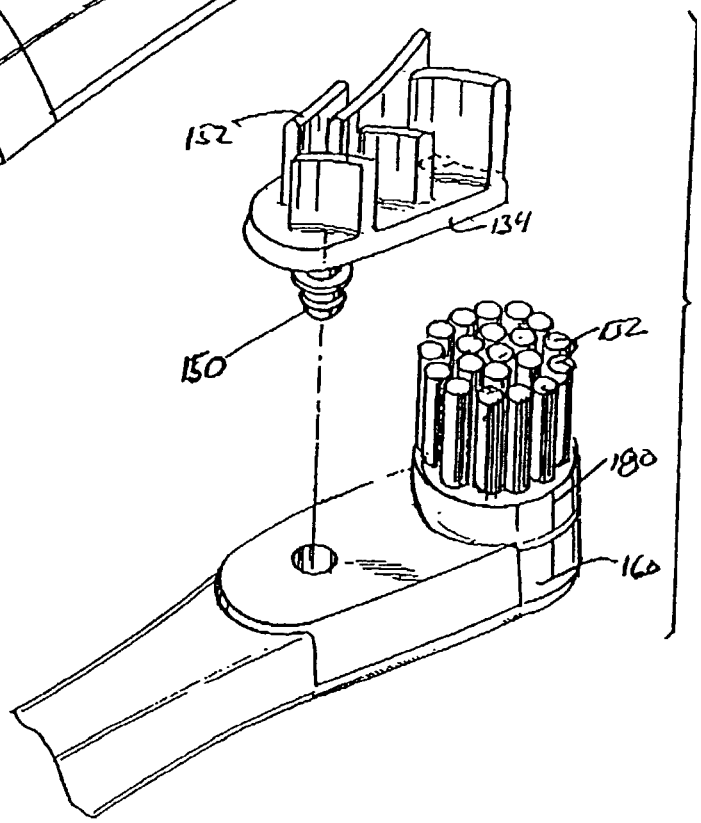
FIG. 15 is a front and side perspective view of another embodiment of a powered toothbrush head of the powered toothbrush of FIG. 2.

FIGS. 14 through 16 illustrate additional exemplary embodiments generating various movements. FIG. 14 illustrates the movement of platform 134 when the leg 150 is located solely at the midpoint 144 of platform 134. Platform 134 will therefore rotate along arrow D, this will impart greater movement to second end 138 of platform. FIG. 15 illustrates an embodiment where leg 150 is pivotally connected to base 160. This will again allow greater movement of second end 138. The above movements will be generated regardless of how the motion from first movable bristle carrier 180 is imparted to platform 134. FIGS. 16A–16C illustrate various positions generated during movement of the constructions illustrated in FIGS. 14 and 15. Both of these constructions include second movable bristle carriers that may rotate about the midpoint 144 thereof, resulting in an increase in the lateral movement of second end 138 of platform 134, as illustrated by arrow E, when first movable bristle carrier 180 oscillates across arrow F.

FIG. 17 illustrates another exemplary head embodiment. Handle 102, neck 110, drive, and head base 160 may be the same as described above. A second movable bristle carrier 232 may be operatively connected to a second drive mechanism that will move second movable bristle carrier 232 in a third direction. The second drive feature may include at least one cam surface 400 that selectively contacts second movable bristle carrier 232 or platform 234 to cause movement, in one preferred embodiment, perpendicular to first movable bristle carrier 128 (in the direction indicated by arrow G).

FIG. 18 illustrates yet another embodiment wherein leg 150 may span from approximately second end 138 to approximately first end 136 of platform 134. This positioning of leg 150 may cause platform 134 to 'rock' back and forth across the longitudinal axis of toothbrush 100, in the directions indicated by arrows H. Leg 150 may also be attached to second movable bristle carrier 132 via a receiving groove 410.

A powered toothbrush made in accordance with any of the present embodiments offers a number of advantages over conventional powered toothbrushes that are presently available. First movable bristle carrier 180 oscillates back and forth, or moves otherwise. As the operator brushes his or her teeth, the oscillating tooth care elements (i.e., bristle tufts and/or elastomeric members) contact the surfaces of the teeth and the surrounding areas to deliver enhanced cleaning, tooth polishing and/or tooth whitening. The elastomeric second bristle carrier 132 permits a number of additional tooth care elements to be disposed in a number of different patterns. The increased number of moving tooth care elements of second bristle carrier provides increased contact with gingival tissues and enhanced massaging thereof.

The toothbrush according to the various embodiments disclosed herein can be made from any number of materials that are suitable for use in oral care products, such as toothbrushes, etc. For example, many of the components that are included in toothbrush are formed of plastic materials. Accordingly, the handle and head of the powered toothbrush may be molded from polyolefins such as polypropylenes and polyethylenes, polyamids such as nylons, and polyesters such as polyethylene terephthalate. Other suitable materials include polymethylmethacrylate, styrene acroylonitrile and cellulose esters, for example cellulose propionate.

When the tooth care elements are in the form of tufts of bristles, the bristles of can be made from a flexible material suitable for dental hygiene. Generally, materials suitable for bristles are polyamides such as nylon or polyesters such as polybutylene terephthalate. When the tooth care elements are in the form of elastomeric members, they can be made from any number of suitable elastomeric materials, such as a block copolymer. Preferred block copolymers include styrenes (for example styrene ethylene butadiene styrene, or styrene butadiene styrene), polyolefins (for example polypropylene/ethylene propylene diamine modified systems (i.e. synthetic rubber)), polyamides (for example polyamide (2 or polyamide 6), polyesters (for example polyester ester or polyether ester), polyurethanes (for, example polyesterurethane, polyetherurethane or polyesteretherurethane).

It will thus be seen that the objects set forth above, among those made apparent from the preceding description, are efficiently attained and, because certain changes may be made in carrying out the above method and in the construction(s) set forth without departing from the spirit and scope of the invention, it is intended that all matter contained in the above description and shown in the accompanying drawings shall be interpreted as illustrative and not in a limiting sense.

It is also to be understood that the following claims are intended to cover all of the generic and specific features of the invention herein described and all statements of the scope of the invention which, as a matter of language, might be said to fall therebetween.

What is claimed is:

1. A powered toothbrush comprising:
   a handle portion and
   a head coupled to the handle portion, the head further including:
   abase;
   a first carrier coupled to the base and operatively connected to a first drive feature for moving the first carrier in a first direction, the first carrier having at least one first cleaning member extending outwardly therefrom; and
   a second carrier coupled to the base, the second carrier having a plurality of second cleaning members separated by a respective spacing and extending outwardly from the second carrier, the second carrier engaging the first carrier so that the movement of the first carrier in the first direction is translated into movement of the second carrier in a second direction;
   wherein the second carrier comprises an elastomeric material such that the spacing between the plurality of second cleaning members changes with the movement of the second carrier.

2. The powered toothbrush as defined in claim 1, wherein the first direction is a direction defined radially about a center point of said first carrier.

3. The powered toothbrush as defined in claim 1, wherein the first carrier oscillates in a back and forth manner.

4. The powered toothbrush as defined in claim 1, wherein the first carrier oscillates in a rotational direction.

5. The powered toothbrush as defined in claim 1, wherein the second direction is a direction defined radially about a center point of said first carrier.

6. The powered toothbrush as defined in claim 1, wherein the second direction is a direction along a longitudinal axis of the head.

7. The powered toothbrush as defined in claim 1, wherein the first carrier comprises a disc shaped member.

8. The powered toothbrush as defined in claim 1, wherein the second carrier includes a platform having at least one leg extending outwardly therefrom to couple the second carrier to the base.

9. The powered toothbrush as defined in claim 8, wherein the at least one leg is formed at an end of the platform that is opposite an end of the platform that is engaged to the first carrier.

10. The powered toothbrush as defined in claim 8, wherein the at least one leg is formed of one of a rigid material and an elastomeric material.

11. The powered toothbrush as defined in claim 8, wherein the platform is formed of one of a rigid material and an elastomeric material.

12. The powered toothbrush as defined in claim 8, wherein said second carrier engages said first carrier in accordance with a protrusion disposed at an end of the platform of the second carrier that faces the first carrier, said first carrier defining a complementary recess to receive the protrusion.

13. The powered toothbrush as defined in claim 12, wherein the protrusion of the platform is rigidly received in the recess.

14. The powered toothbrush as defined in claim 12, wherein the protrusion of the platform is frictionally received in the recess.

15. The powered toothbrush as defined in claim 8, wherein said second carrier engages said first carrier in accordance with an elastomeric member that extends outwardly from an end of the platform of the second carrier that faces the first carrier and is received within a complementary recess defined by the first carrier such tat when the first carrier moves in the first direction, the elastomeric member remains in the recess, resulting in the second carrier moving in the second direction.

16. The powered toothbrush as defined in claim 1, wherein the first drive feature comprises a drive shaft that is part of a drive mechanism.

17. The powered toothbrush as defined in claim 1, wherein the first direction and the second direction are the same.

18. The powered toothbrush as defined in claim 1, wherein the second carrier is coupled to the base by a first leg that is formed at one of a midpoint of a first end of the second carrier that faces and is adjacent the first carrier and a midpoint of a second end that is opposite the first end and positioned apart from the first carrier.

19. The powered toothbrush as defined in claim 18, wherein the second earner moves in the second direction about the first leg.

20. The powered toothbrush as defined in claim 18, wherein the second carrier includes a second leg that is disposed at a midpoint of an end of the second carrier opposite the end at which the first leg is disposed.

21. The powered toothbrush as defined in claim 1, wherein said second carrier engages said first carrier in accordance with a recess defined by the second carrier at a location which faces the first carrier and a member coupled to said first carrier that is received into the recess.

22. The powered toothbrush as defined in claim 21, wherein the recess is formed in an end wall that faces the first carrier and the member comprises a protrusion that extends outwardly from the first carrier.

23. The powered toothbrush as defined in claim 22, wherein the protrusion is formed of a rigid material and the second carrier is formed of an elastomeric material to permit movement of the first carrier to be translated into movement of the second carrier through movement of the protrusion.

24. The powered toothbrush as defined in claim 1, wherein the second carrier is an elastomeric body disposed proximate to the first carrier, the second carrier having at least one surface that faces the first carrier and the first carrier including an edge that selectively contacts the at least one surface when the first carrier moves in the first direction, resulting in the second carrier being moved in the second direction.

25. The powered toothbrush as defined in claim 24, wherein a first end of the second carrier faces the first carrier, the at least one surface being a lateral section of the first end and the edge of the first carrier that selectively contacts the at least one surface is in the form of an extension protruding outwardly from the first carrier.

26. The powered toothbrush as defined in claim 1, wherein the movement in the second direction comprises rotation about a member that couples the second carrier to the base, said movement being lateral to the first carrier.

27. The powered toothbrush as defined in claim 1, wherein the movement in the second direction comprises rotation about a member that couples the second carrier to the base, said movement being longitudinal and lateral relative to the first carrier.

28. The powered toothbrush as defined in claim 1, wherein the second carrier is operatively connected to a second drive feature for moving the second carrier in a third direction different from the first and second directions.

29. The powered toothbrush as defined in claim 28, wherein the third direction is a direction perpendicular to a surface of the base.

30. The powered toothbrush as defined in claim 28, wherein the second drive feature comprises at least one cam surface that selectively contacts the second carrier to cause movement of the second carrier in the third direction.

31. The powered toothbrush as defined in claim 30, wherein the second carrier includes a platform that is operatively connected to the second drive feature for moving the second carrier in the third direction, the at least one cam surface selectively contacting a bottom surface of platform to cause movement of platform in the third direction.

32. A powered toothbrush comprising:
a handle portion and
a head coupled to handle portion, the head further including:
a first carrier coupled to the head and operatively connected to a first drive feature for moving the first carrier in a first direction, the first carrier having at least one first cleaning member extending outwardly therefrom; and
a second carrier coupled to the head at a first location, the second carrier being an elastomeric member in selective contact with the first carrier at a second location such that movement of the first carrier imparts movement to the second carrier, the second carrier having a plurality of second cleaning members extending outwardly from an upper surface thereof, wherein a spacing between the plurality of second cleaning members on the second carrier changes with the movement of the second carrier.

33. A powered toothbrush comprising:
a handle portion and
a head coupled to the handle portion, the head further including:
a first carrier coupled to the head and operatively connected to a first drive feature for moving the first carrier in a first direction, the first carrier having at least one first cleaning member extending outwardly therefrom; and
a second carrier including a member that couples the second carrier to the head, the second carrier having a section that extends outwardly therefrom and engages the first carrier such that movement of the first carrier in the first direction is translated into movement of the second carrier in a second direction, the second carrier having at least a plurality of elastomeric cleaning members spaced from each other by a spacing and extending outwardly from the second carrier,
wherein the spacing between the plurality of elastomeric cleaning members on the second carrier changes with the movement of the second carrier.

34. The powered toothbrush as defined in claim 33, wherein the second carrier pivots about the member when the second carrier moves in the second direction.

35. The powered toothbrush as defined in claim 33, wherein the member comprises at least one leg extending from the second carrier and being attached to the head.

36. The powered toothbrush as defined in claim 33, wherein the section comprises a protrusion that is received within a recess defined by the first carrier, the protrusion being retained in the recess when the first carrier moves in the first direction.

37. The powered toothbrush as defined in claim 33, wherein the second carrier includes an upstanding elastomeric wall extending outwardly from an upper surface, the upstanding elastomeric wall having a shape selected from the group consisting of linear, zigzag, and serpentine.

38. A brush section for use in a powered toothbrush having a handle portion, the brush section comprising:
a head adapted to be coupled to the handle portion, the head further including:
a first carrier coupled to the head and operatively connected to a first drive feature for moving the first carrier in a first direction, the first carrier having at least one first cleaning member extending outwardly therefrom; and
a second carrier coupled to head, the second carrier having a plurality of second cleaning members separated by a spacing and extending outwardly from the second carrier, the second carrier engaging the first carrier so that the movement of the first carrier in the first direction is translated into movement of the second carrier in a second direction;
wherein the spacing between the plurality of second cleaning members changes with the movement of the second carrier.

* * * * *